United States Patent
Scheinberg et al.

(10) Patent No.: US 7,479,577 B2
(45) Date of Patent: Jan. 20, 2009

(54) FRICTION REDUCING DEVICES

(75) Inventors: Samuel Scheinberg, Otis, OR (US);
Adrian A. Polliack, Lake Oswego, OR (US)

(73) Assignee: Advanced Wound Systems, LLC, Newport, OR (US)

( * ) Notice: Subject to any disclaimer, the term of this patent is extended or adjusted under 35 U.S.C. 154(b) by 0 days.

(21) Appl. No.: 11/501,670

(22) Filed: Aug. 8, 2006

(65) Prior Publication Data

US 2007/0027423 A1 Feb. 1, 2007

Related U.S. Application Data

(63) Continuation-in-part of application No. 10/672,731, filed on Sep. 25, 2003, now Pat. No. 7,087,806, which is a continuation-in-part of application No. 10/637,429, filed on Aug. 8, 2003, now abandoned.

(51) Int. Cl.
*A61F 13/00* (2006.01)
*A61F 5/37* (2006.01)

(52) U.S. Cl. .......................... 602/58; 602/42; 128/882; 128/889

(58) Field of Classification Search .................. 2/69; 602/41–43, 52, 57, 58; 604/271; 128/845, 128/882, 889, 893, 894
See application file for complete search history.

(56) References Cited

U.S. PATENT DOCUMENTS

| 1,913,928 | A | 6/1933 | Kaufman |
|---|---|---|---|
| 2,098,312 | A | 11/1937 | Scholl |
| 2,261,041 | A | 10/1941 | Tennant |
| 2,669,989 | A | 2/1954 | Shoucair |
| 2,712,311 | A | 7/1955 | Scholl |
| 2,817,335 | A | 12/1957 | Thompson |
| 2,918,062 | A | 12/1959 | Scholl |
| 3,062,208 | A | 11/1962 | Scholl |
| 3,260,261 | A | 7/1966 | Gallovich |
| 3,548,420 | A | 12/1970 | Spence |
| 3,821,954 | A | 7/1974 | Grubel |
| 3,968,530 | A | 7/1976 | Dyson |
| 4,572,174 | A | 2/1986 | Eilender et al. |
| 4,600,001 | A | 7/1986 | Gilman |
| 4,729,369 | A | 3/1988 | Cook |
| 4,959,059 | A | 9/1990 | Eilender et al. |
| 5,012,801 | A | 5/1991 | Feret |
| RE33,727 | E | 10/1991 | Sims |
| 5,170,781 | A | 12/1992 | Loomis |
| 5,188,124 | A | 2/1993 | Feret |

(Continued)

FOREIGN PATENT DOCUMENTS

EP 0051935 A2 5/1982

*Primary Examiner*—Kim M. Lewis
(74) *Attorney, Agent, or Firm*—Chernoff, Vilhauer, McClung & Stenzel, LLP

(57) ABSTRACT

Devices for reduction of damage from friction and for prevention and treatment of skin breakdown by relief of friction and shear forces. A friction reducing device may include a pair of thin membranes with low coefficients of friction with respect to each other, and of which one is free to slide through a limited distance along the other. A method of making one such device includes forming a dome in a flexible film and adhesively attaching a skirt surrounding the dome to a skin contact layer. Similar friction reducing devices may be incorporated in shoes, other clothing, or sports equipment or used to protect movable rods or cables.

18 Claims, 13 Drawing Sheets

U.S. PATENT DOCUMENTS

| | | |
|---|---|---|
| 5,462,519 A | 10/1995 | Carver |
| 5,665,060 A | 9/1997 | Fabricant |
| 5,899,207 A | 5/1999 | Scheinberg |
| 6,067,987 A * | 5/2000 | Scheinberg ................ 128/882 |
| 6,169,224 B1 | 1/2001 | Heinecke et al. |
| 6,320,093 B1 | 11/2001 | Augustine et al. |
| 6,916,967 B2 * | 7/2005 | Wright et al. ................ 602/42 |
| 2005/0033212 A1 | 2/2005 | Scheinberg et al. |
| 2007/0043316 A1 * | 2/2007 | Carlson et al. ................ 602/41 |

* cited by examiner

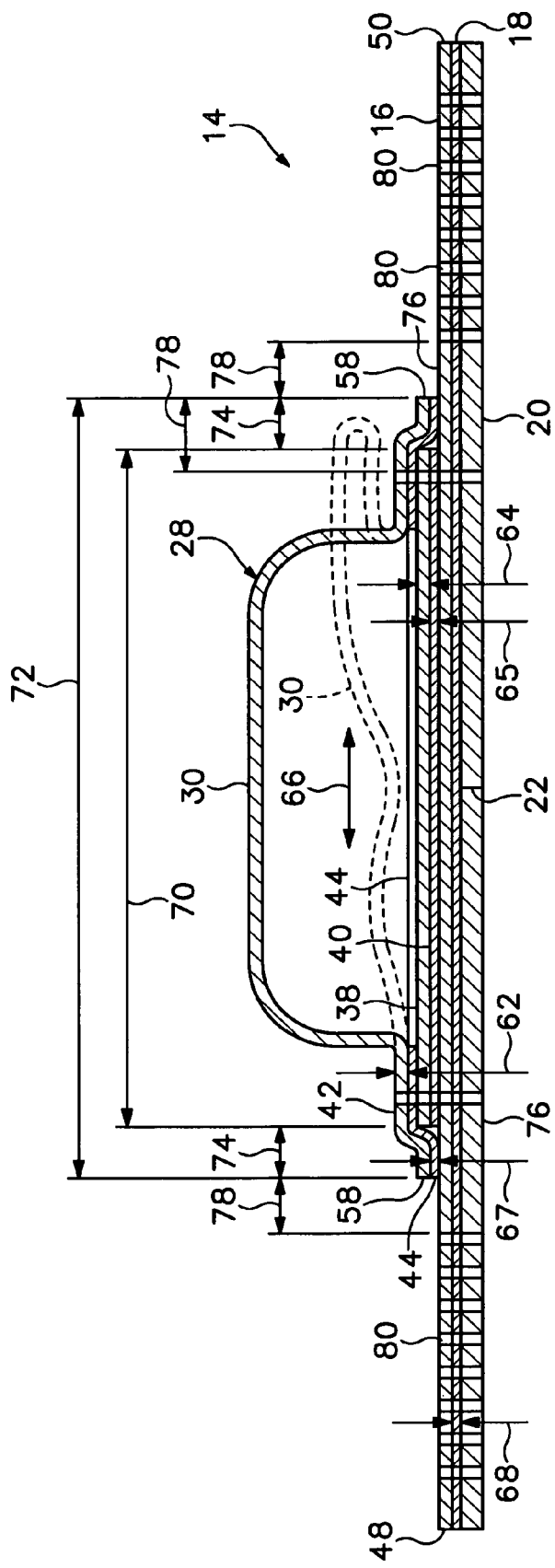
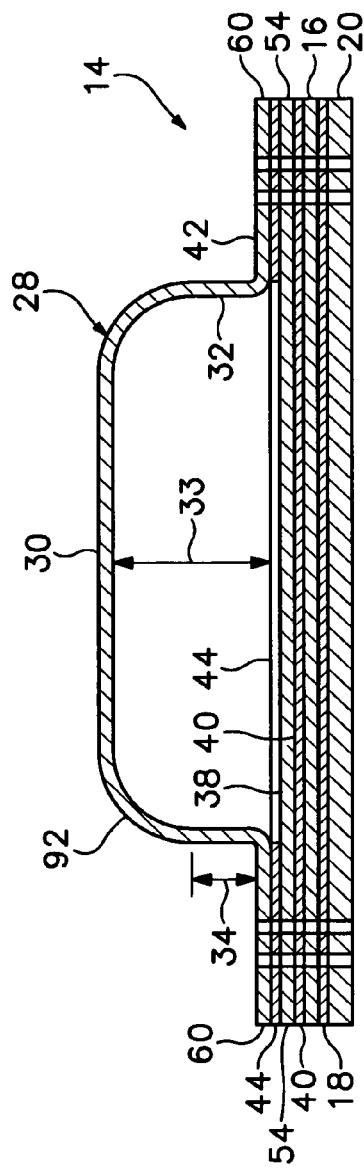
FIG.3
FIG.4

Fig. 21
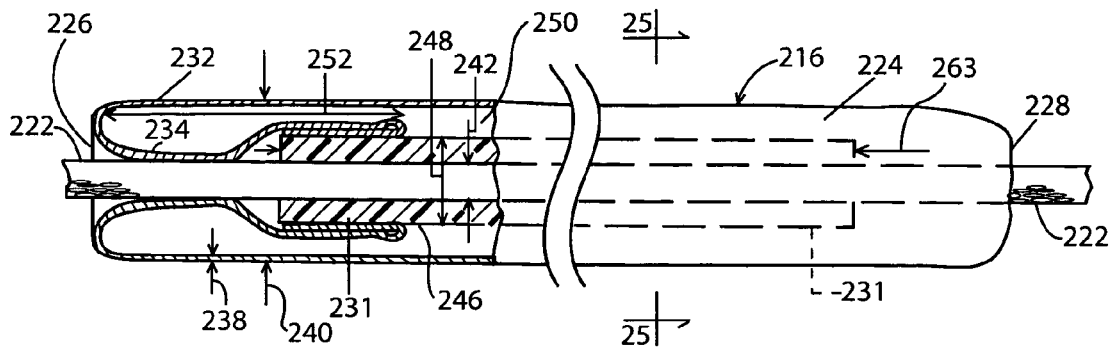
Fig. 22
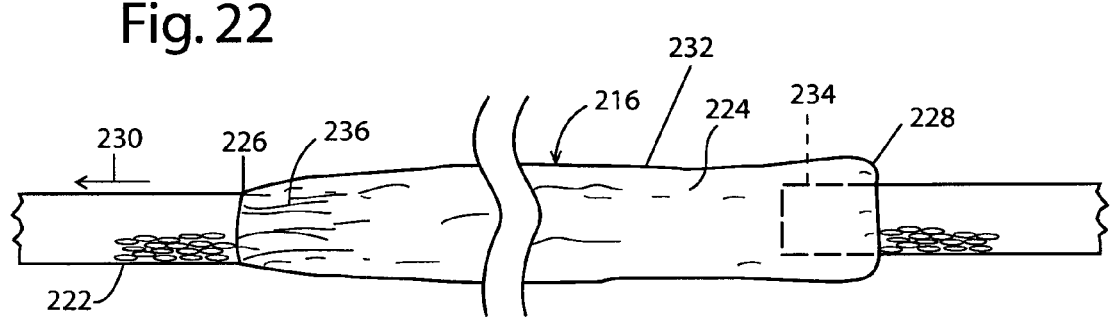
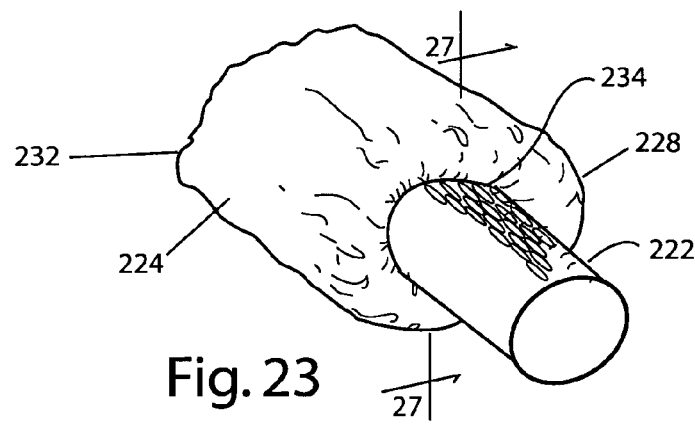
Fig. 23

FRICTION REDUCING DEVICES

CROSS-REFERENCE TO RELATED APPLICATIONS

This application is a continuation-in-part of U.S. patent application Ser. No. 10/672,731, filed Sep. 25, 2003 now U.S. Pat. No. 7,087,806, which is a continuation-in-part of application Ser. No. 10/637,429, filed Aug. 8, 2003 now abandoned.

BACKGROUND OF THE INVENTION

The present invention relates to reduction of friction and prevention and treatment of irritation, discomfort, pain and skin breakdown resulting from shear and friction forces and pressure against a moving object.

Friction and shear forces are two factors that play a significant role in causing breakdown of skin and the underlying tissues, which can lead to erythema (red spots), blisters and pressure ulcers. Friction and shear forces commonly occur at the skin-support interface, e.g. where the skin contacts another surface such as in malfitting footwear, bedding, wheelchairs, under casts and under the socket of a prosthesis (artificial limb). Skin breakdown can also occur following rubbing on skin areas contacted by undergarments, athletic equipment, and clothing, skin of hands operating industrial equipment and machinery, and in many other instances where repeated rubbing of skin occurs. The present invention relates to reducing the friction and shear forces contributing to these disabling and serious conditions.

Scheinberg U.S. Pat. Nos. 5,899,207 and 6,067,987 disclose a tissue-protective device including mutually overlying membranous layers arranged to be able to slip easily along each other at the interface between the skin and an adjacent surface, e.g. a shoe, another article of clothing or equipment pressing against or moving along the surface of skin, and internally between soft tissues in vivo, for protection from friction. The devices disclosed by Scheinberg, however, are not particularly well adapted for mass production.

What is desired, then, is a dressing or bandage which can readily be mass-produced in a form easily used by application to a person's skin or by incorporation in an article of clothing or other article that may cause friction, shearing, or pressure on the skin, either to prevent skin breakdown and reduce irritation, discomfort and pain, or to protect and enhance healing of an area of a person's skin which has already been damaged by rubbing and pressure. Preferably such an improved device should be thin, in order to avoid creating additional pressure to the skin and underlying tissues, while greatly reducing shear and friction forces encountered by the skin. Such a bandage should be flexible, so that it can be easily contoured to complex curvatures of anatomical sites such as the heel, ankles and elbows. It should also be able to stretch and move with the skin during activity.

Also desired is a protective friction reducing device for use in other circumstances where articles in contact with each other may frequently be moved in either direction from a central location. Such a device should be of simple construction, yet durable.

A method for economically making such a dressing, bandage, or other friction reducing device is also needed.

SUMMARY OF THE INVENTION

The present invention provides a bandage that overcomes some of the shortcomings of previously available devices for protecting a person's skin from injury or irritation, and also provides a friction reducing device for protecting moving articles, especially slender objects that move reciprocatingly, and a method of manufacturing such protective friction reducing devices.

In one embodiment of the protective bandage a skin contact layer is of a flexible film. A hollow dome of flexible film is attached to the skin contact layer and is free to move along the skin contact layer through a distance related to the height of the dome, while the side of the layer opposite the dome can be attached to a person's skin by an adhesive.

In one embodiment of the bandage, the dome may include a dome top layer of flexible film defining the shape of the dome, and a substantially flat dome base layer of similar film material. The dome top layer is attached to the dome base layer, so that the dome top layer can slide along the surface of the dome base layer and the dome base layer is attached directly to the skin contact layer.

As a feature of one embodiment of the bandage, the skin contact layer may be of a flexible film material which is more elastic than the film material of the dome, and the skin contact layer may extend beyond the dome to attach the dome securely to a person's skin, yet conform to and stretch and relax with the skin to which it is attached as the person moves.

In one embodiment of the bandage, the skin contact layer may be perforated, to enhance moisture and vapor transfer from the person's skin, and add to flexibility of the skin contact layer. Perforation may be omitted near a boundary between the material defining the dome and the portions of the skin contact layer that extend beyond the dome material.

In one embodiment, the friction reducing structure may be incorporated in an article of clothing or sports equipment against which a person's skin may be in frequent contact.

In one embodiment, a friction reducing device may be attached to and extend around and along a portion of the length of an elongate force-carrying element such as a rod, control wire, or cable, to protect against frictional wear on the rod, wire, or cable or reduce the amount of force necessary to move such an element during operation of a mechanical device.

A method of making a bandage according to the invention may include forming a flexible dome including a side wall in a flexible film, leaving the dome surrounded by a generally planar skirt, and thereafter attaching the skirt adhesively to a skin contact layer of flexible film.

A method of manufacturing a bandage according to the present invention may include defining openings corresponding with the size of domes for the bandages in a sheet of transfer adhesive material, applying the transfer adhesive to a web of flexible film material, thereafter forming the film material within the openings to define domes, and thereafter using the adhesive layer to attach each dome to a layer of film material.

A method for manufacturing a friction reducing device for use on a cable, wire, or rod may include first fastening a tubular inner element in place surrounding a portion of the length of a cable, wire, or rod, and thereafter fastening a tubular outer layer in place about the inner element in such a way that there is freedom for the outer layer to move with respect to the inner element.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

FIG. 3 is a section view taken on line 3-3 of FIG. 2 with thicknesses greatly exaggerated.

FIG. 4 is a section view taken on line 4-4 of FIG. 2 with thicknesses greatly exaggerated.

FIG. 21 is a foreshortened, partially cutaway side elevational view of a length of cable equipped with a friction reducing protective device similar to that shown in FIG. 20.

FIG. 22 is a foreshortened side elevational view of the portion of a cable shown in FIG. 21, at a somewhat enlarged scale, showing the friction reducing protective device after the cable has been moved in a leftward direction.

FIG. 23 is a perspective view of the right end of the portion of a cable and friction reducing protective device shown in FIG. 22.

DETAILED DESCRIPTION OF PREFERRED EMBODIMENTS

Figure 1:
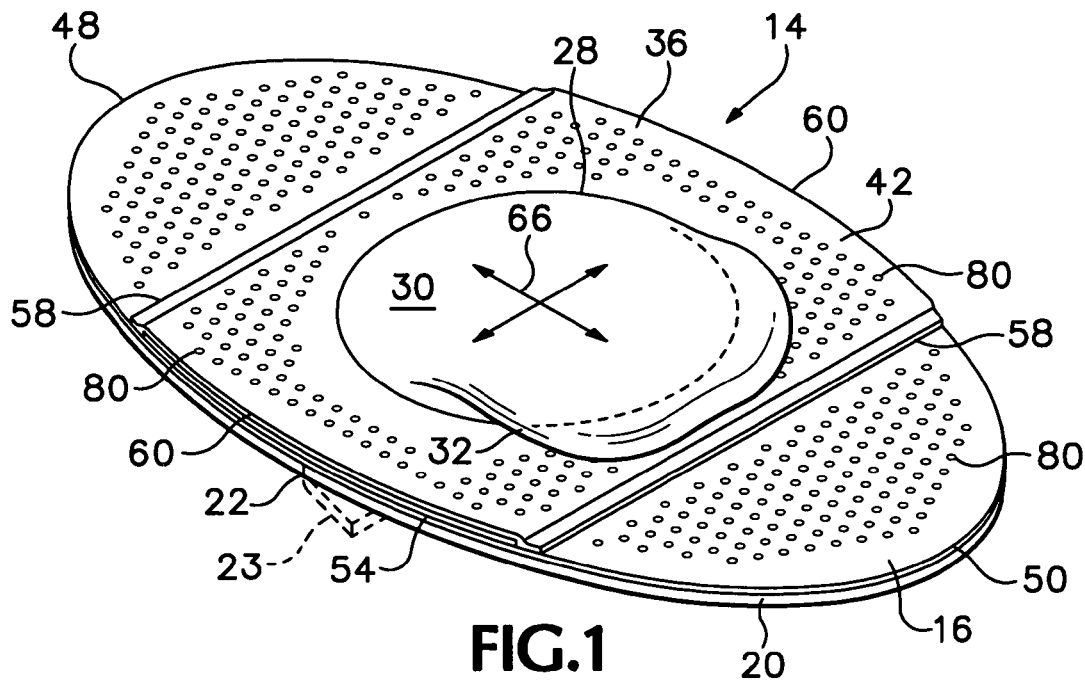
FIG. 1 is a perspective view of a bandage which is an embodiment of one aspect of the present invention.
Figure 2:
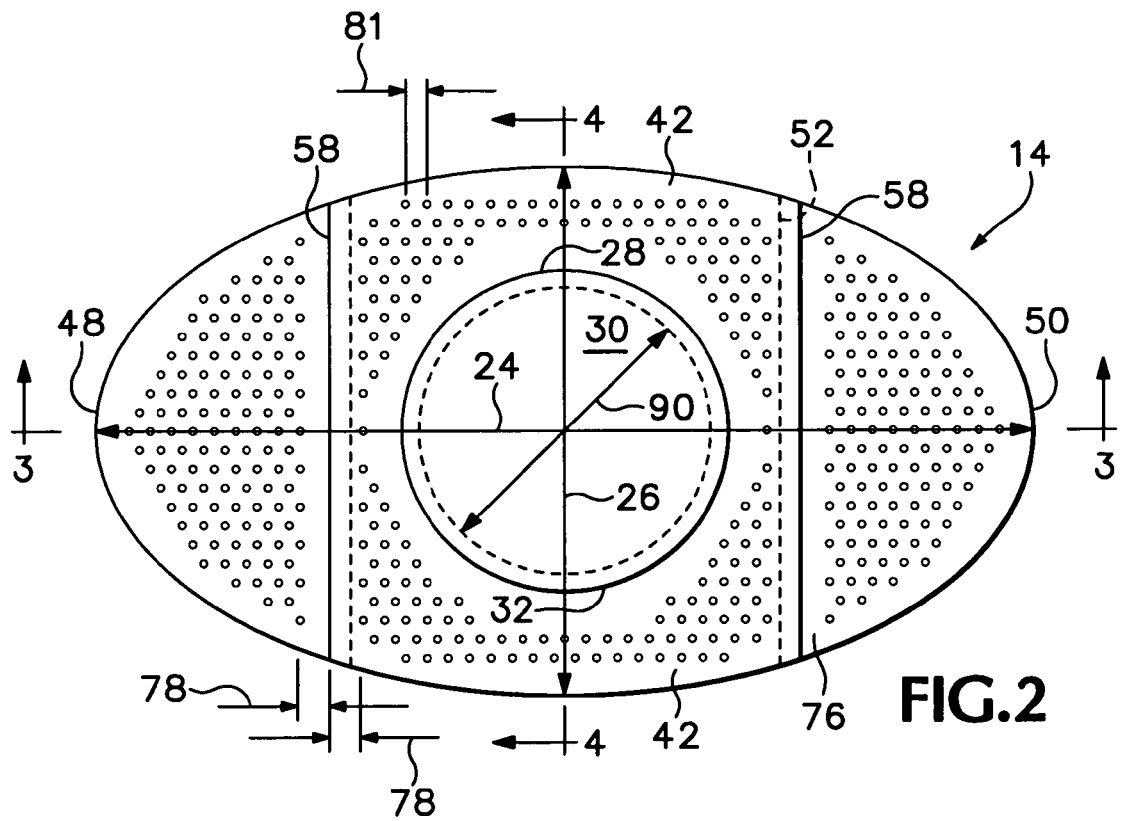
FIG. 2 is a top plan view of the bandage shown in FIG. 1.
Figure 5:
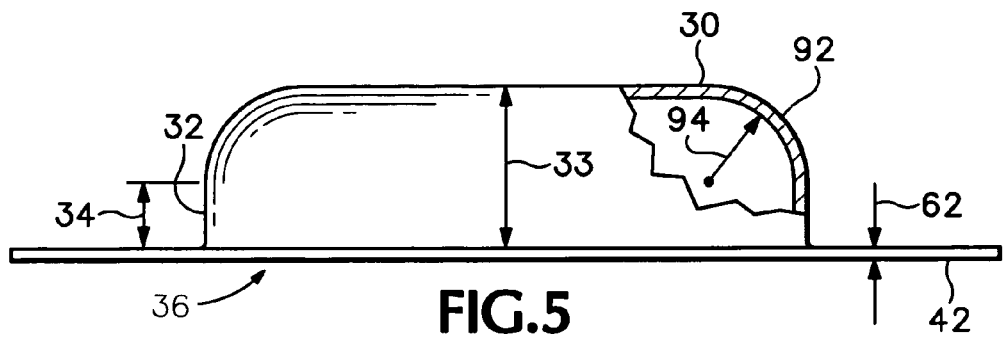
FIG. 5 is a partially cutaway sectional detail view of the dome top layer of the bandage, taken in the direction indicated by line 4-4 of FIG. 2.

Referring to FIGS. 1-4 of the drawings which form a part of the disclosure herein, an elliptical bandage 14 which is one preferred embodiment of the present invention includes a skin contact layer 16 of flexible film material to which a layer 18 of an adhesive material is adhered. The layer 18 of adhesive material is protected by an easily removable liner 20 divided into two separate halves by a cut 22 extending across the liner 20 to allow the halves of the liner 20 to be removed separately during application of the bandage 14 to a person's skin. Alternatively, one part of the liner 20 can overlap the other along the location of the cut 22, with the overlying portion including a folded-back margin flap 23 shown in broken line, to facilitate removal of the liner 20 from the skin contact layer 20 to apply the bandage. As one preferred size, the bandage 14 may have a length 24 of 66.67 mm (2.625 in.) and a width 26 of 38.1 mm (1.5 in.).

A dome 28 is centrally located on and adhesively attached to the skin contact layer 16. The dome 28 includes a top portion 30 and a circumferential side wall portion 32 interconnecting the top portion with the skin contact layer 16 and with intermediate portions of the bandage 14, as will be described in more detail presently. The dome 28 is of a thin, strong, flexible, film material, and its top portion 30 is free to move parallel with the skin contact layer 16 in any direction from a neutral position, as limited principally by the height 33 of the side wall portion 32 of the dome. The dome may have a diameter 29 of 25.15 mm (0.990 in.), and the top portion 30 may have a diameter 31 of 22.86 mm (0.0900 in.), for example, and the dome 28 may have a height 33 of 4.76 mm (0.1875 in.).

As shown in FIGS. 2-5, in the preferred embodiment of the bandage 14, the dome 28 includes a dome top layer 36 and a dome base layer 38. The dome base layer 38 is fastened to a first, or upper, side of the skin contact layer 16, for example being adhesively attached by a layer of adhesive material 40 that is coextensive with the dome base layer 38. As used herein, the term adhesively attached should be understood to include the use of various mechanisms such as thermal fusion, ultrasonic fusion, and chemical fusion to interconnect layers of the bandage 14, as well as the use of layers of adhesive materials such as the particular pressure sensitive adhesives described herein in detail.

The dome top layer 36 includes the top portion 30, the side wall portion 32, and a skirt portion 42 that is generally flat and which surrounds and extends radially outward in all directions from the base of the side wall portion 32. The skirt portion 42 is adhesively attached to the dome base layer 38 and the skin contact layer 16, as by a layer 44 of adhesive material. The layer 44 of adhesive material is coextensive with the skirt portion 42 but does not extend onto the side wall portion 32 or the top portion 30 of the dome 28.

The skin contact layer 16 is larger than either the dome base layer 38 or the dome top layer 36 and preferably has an elliptical or other elongated oval shape, extending away from the dome 28 in both of a pair of opposite directions to opposite ends 48 and 50. Other shapes could also be useful for use of the bandage 14 in a particular place.

The dome base layer 38 has a pair of opposite and parallel straight margins 52 extending transversely across the skin contact layer 16, while arcuate opposite ends 54 of the dome base layer 38 coincide with portions of the side margins 56 of the skin contact layer 16. The skirt portion 42 of the dome top layer 36 similarly has a pair of parallel straight margins 58 and a pair of arcuate opposite ends 60 which also coincide with portions of the side margins 56 of the skin contact layer 16.

The straight margins 58 of the dome top layer 36 are separated from each other by a distance 72 that is somewhat greater than the distance 70 between the parallel straight margins 52 of the dome base layer 38, so that each straight margin 58 extends beyond the adjacent straight margin 52 toward a respective nearer one of the opposite ends 48 and 50 of the skin contact layer 16 on either end of the bandage 14. For example, the width 70 of the dome base layer 38 between its straight margins 52 is preferably 28.6 mm (1.125 in.), while the width 72 of the dome top layer 36 may be 31.75 mm (1.25 in.), so that a portion of the skirt portion 42 attached to the skin contact layer 16 overlaps the dome base layer 38 on each side by a width 74 of about 1.6 mm (0.0625 in) beyond the straight margin 52. The adhesive layer 44 thus attaches the dome top layer 36 both to the dome base layer 38, in an area surrounding the dome 28, and to the first or upper side of the skin contact layer 16, in narrow areas between the straight margins 52 and 58, between the dome 28 and each of the opposite ends 48 and 50 of the skin contact layer 16. This arrangement with the margins 58 of the skirt portion 42 overlapping beyond the margins 52 provides a smooth contour of the bandage 14 in the connection of the dome top layer 36 to the skin contact layer 16, and adds to security of the connection of the dome 28 to the skin contact layer 16.

Since the adhesive layer 44 is present only on the skirt portion 42 of the dome top layer 36, the top portion 30 of the dome is free from the opposing upper surface of the dome base layer 38. The top portion 30 thus can move parallel with and along the upper surface of the dome base layer 38 in any direction in which it is urged, to the extent that it is permitted to move by the height 33 of the side wall portion 32. The thin film material of the dome top layer 36 and dome base layer 38 is a flexible and strong membrane, and has a low enough coefficient of friction, when rubbing against surfaces of similar material, that there is significantly less friction between the top portion 30 of the dome and the dome base layer 38 than is likely between, for example, a person's skin and a sock pressed against the skin by the inside of a shoe.

The film of which the dome top layer 36 may also be somewhat pervious to gas, so that the dome 28 can inflate, deflate, or collapse, according to the design of a particular dome, and particular material used as the dome top layer 36. The top portion 30 can contact and move in any direction along the dome base layer 38 (or the skin contact layer 16, should there be no dome base layer 38), as indicated by the arrow 66. Thus, while the dome 28 is shown in a neutral position in FIGS. 2-5, it is shown in FIG. 1 in a collapsed condition and offset toward the end 50 of the base layer 16, as also indicated in broken line in FIG. 3.

In order to protect a portion of a person's skin exposed to pressure or rubbing without adding to potential irritation, the entire bandage 14 is flexible and preferably as thin as practical consistent with sufficient strength. Accordingly, the dome top layer 36 may be of polyethylene film having a thickness 62 of about 25 microns (1 mil), and the dome base layer 38 is preferably of similar film material also having a thickness 64 of about 25 microns (1 mil). In such a small thickness, the polyethylene is amply flexible yet strong enough to withstand the usual forces to be encountered. A suitable polyethylene film is available in such a thickness from Quality Extrusion of Mankato, Minn., as its QCE 5% EVA type A polyethylene film.

Preferably, the adhesive layers 40 and 44 respectively interconnecting the dome base layer 38 with the skin contact layer 16 and interconnecting the skirt portion 42 of the dome top layer 36 with the dome base layer 38 and the skin contact layer 16 have similar thicknesses 65 and 67 of about 25 microns (1 mil). One suitable transfer adhesive is a non-sensitizing medical grade, biocompatible transfer adhesive, available from Tyco Adhesives of Norwood, Mass., as its "TR 2295C Medical Grade Transfer Adhesive," in the form of a coiled transfer tape, a web of adhesive material carried on a backing or liner that is relatively easily removable after the adhesive is mated with the polyethylene film material of either the dome top layer 36 or the dome base layer 38.

A suitable material for the skin contact layer 16 is a polyurethane film having a thickness 68 of about 50 microns (2 mils). Such a polyurethane film is suitably strong and flexible and also is slightly more elastic than polyethylene, and thus is more able to conform to a person's skin as the skin stretches and relaxes during movement, than the polyethylene material preferred for the dome top layer 36 and base layer 38.

An acceptable polyurethane film for use as the skin contact layer 16 is available from Avery Dennison Medical, of Mentor, Ohio, in such a thickness, together with a non-sensitizing, pressure sensitive, acrylic co-polymer adhesive coating on one face of the film and ready for use as the adhesive layer 18, and with a silicone coated kraft paper liner already adhered to the layer 18 of adhesive material. Such a laminated material is available from Avery Dennison Medical as its MED 5042 polyurethane film.

The bandage 14 in use thus has a thickness (excluding the liner 20) of not more than about 0.15 mm (6 mils), so as to avoid aggravating pressure on one's skin by added bulk, as inside a shoe, for example.

For still thinner bandages, one may use materials chosen to have a low coefficient of friction between the dome top layer 36 and the skin contact layer 16, or may include a small amount of suitable lubricant (not shown) between the dome top layer 36 and the skin contact layer 16. In this configuration, the dome base layer 38 might be omitted, although this may require a compromise with respect to either the ability of the dome 28 to move easily with respect to the skin contact layer 16, or to the ability of the skin contact layer 16 to conform to the user.

The bandage 14 is preferably perforated to aid in transmission of vapor and moisture from the skin to which the bandage 14 may be attached. Such perforation may also enhance the flexibility of the skin contact layer and its ability to stretch. Arrays of perforations 80 are preferably present within the opposite end portions 48 and 50 and within the skirt portion 42, but perforations may or may not be present in the dome 28 itself. Perforations 80 are preferably separated by only a small spacing 81, such as 1.27 mm (0.050 in.), and preferably in the range of 0.76-2.28 mm (0.030-0.090 in). An area 76 extending along each of the straight margins 58 of the dome top layer 36 is preferably free from perforations, in order to avoid interference with the stability of adhesive attachment of the dome 28 to the skin contact layer 16. For example, an area 76 extending for a distance 78 of about 1.6 mm (0.0625 in) on either side of each of the straight margins 58 is left free from perforations 80 in the bandage 14 described herein above.

Figure 6:
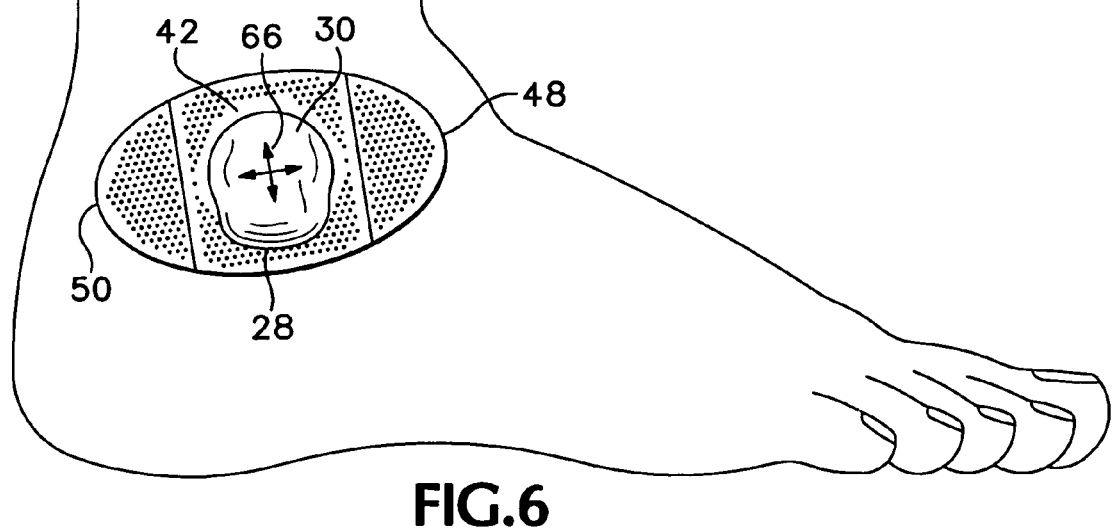
FIG. 6 is a view showing the bandage shown in FIG. 1 in place on a person's ankle.

The bandage 14 can be applied to a person's skin with the dome 28 aligned with a portion of the skin which otherwise might be rubbed by an article interfacing with the person's skin, such as a wheelchair, bedclothing, shoes, athletic equipment, etc. As shown in FIG. 6, the dome 28 is aligned with the prominence on the outside of a person's ankle, and the top portion 30 of the dome 28 is free to move relative to the skirt 42 and the underlying dome base layer 38, while the skin contact layer 16 is securely attached to the person's skin by its adhesive layer 18. The flexibility and elasticity of the skin contact layer 16 permit it to conform easily to the person's ankle, and to stretch and retract itself as the person undergoes activity. The top portion 30 of the dome 28 is free to move in any direction, as indicated by the arrow 66, within the limitations imposed by the height of the dome 28, as previously explained.

Figure 7:
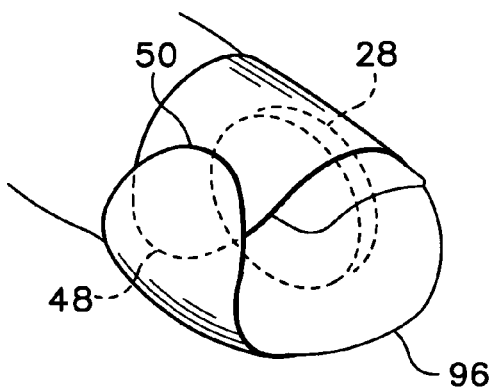
FIG. 7 is a perspective view of the bandage shown in FIG. 1, in place on a person's toe.

The length 24 of the bandage 14, or another bandage of like construction but different size, is intended to permit the opposite ends 48 and 50 of the skin contact layer 16 to overlap one another as shown in FIG. 7 when the bandage is applied to a body part such as a finger or the toe 96, in order to securely hold the bandage in place with the dome 28 located where it is needed to reduce shear and friction forces for prevention or treatment of skin breakdown.

Figure 8A:
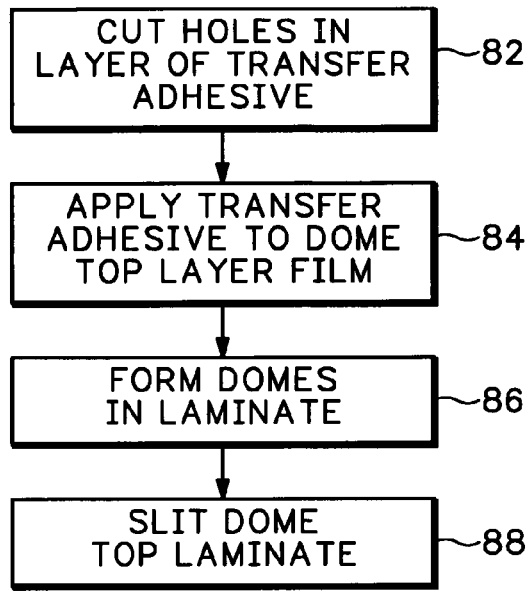
FIG. 8A is a flow diagram showing steps involved in manufacturing a dome top portion for the bandage shown in FIG. 1.

Referring to FIG. 8A, a friction reducing bandage such as the bandage 14 is preferably made using known production equipment for working with films of plastics or other webs of material, performing a novel combination of steps. As a first step, shown at 82 in FIG. 8, domes 28 are prepared by cutting openings corresponding to the size and shape of the dome 28 in a web of a transfer adhesive material to form the adhesive layer 44. The web of transfer adhesive material includes an easily released protective carrier sheet or liner of coated paper on at least one side of a layer of adhesive material. Once the openings have been cut in the layer of transfer adhesive material, the transfer adhesive is adhered to one side of a web of the 1 mil. polyethylene film material for the dome top layer 36, forming a laminate of the dome top layer 36, the layer 44 of adhesive, and the coated paper carrier, as indicated at 84. These first two steps may both be accomplished using a rotary converter apparatus such as, for example, the Crusader® Converter available from Delta Industries of Minneapolis, Minn., or an equivalent converter apparatus capable of unwinding, separating, guiding, combining, and rewinding multiple webs from individual spools while maintaining required alignments and registrations among the various webs.

Thereafter, as noted at 86, a dome 28 is formed in the dome top layer 28 within each opening through the layer 44 of adhesive, using heat and pressure to shape the polyethylene or other polymeric film. The domes 28 may be formed in sequentially produced arrays of several domes 28 produced simultaneously with each application of heat and pressure, using a machine such as is ordinarily used to form considerably thicker sheets of plastics materials to produce clam shell packaging. One such machine which has been found suitable for forming the very thin polyethylene film of the dome top layer 36 to produce an array of domes 28 and their skirts 42 for twenty-seven bandages 14 in each heating and pressing cycle is available from Preco Industries, Inc. of Lenexa, Kans., as its ConvertaForm™ forming system. This machine utilizes appropriate heated molds and dies in an automated air pressure forming system and can handle a forming area up to about 330×420 mm (13 inches by 16.5 inches) with each cycle. For the bandage 14, such domes are prepared using a tool to produce a dome initially having a height 33 of 0.250 in., including a flat top portion 30 with a diameter 31 of 0.900 in., interconnected with the side wall portion 32 by a radiused transition zone 92 whose radius 94 is preferably 0.125 in. but which may satisfactorily be within the range of 1.27-3.81 mm (0.050-0.150 in.). After formation of the domes 28, the polyethylene material typically retracts slightly so that the dome height 33 is ultimately about 4.76 mm (0.1875 in). The domes 28 are thus left free to move in any direction along the dome base layer 38, within the limitations established by the height 34 of the side wall portion 32, the extent of the transition zone 92, and the flexibility of the material of the dome top layer 36.

Instead of the top portion 30 being flat, it may also be formed to extend, for example, in the form of a portion of a spherical surface without adversely affecting the properties of the completed bandage 14.

After the domes 28 have been formed in the laminate of polyethylene dome top layer 36 and layer 44 of transfer adhesive material, the laminate is slit, as mentioned at 88, to form a continuous web of the laminate of the dome top layer 36 with domes 28 formed therein, the adhesive layer 44, and its cover sheet (not shown), bounded by the straight margins 58, and with the width 72 previously mentioned.

Figure 8B:
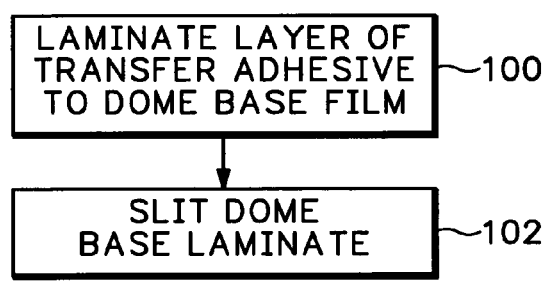
FIG. 8B is a flow diagram showing steps involved in assembling a dome base portion for the bandage shown in FIG. 1.

Referring next to FIG. 8B, using a rotary converter such as that previously mentioned, a layer of transfer adhesive to form adhesive layer 40 is laminated to a web of film material to be used as the dome base layer 38 as shown at 100. As shown at 102 the laminate of the dome base layer film and transfer adhesive is slit to form straight margins 52 separated by the required width 70.

Figure 9:
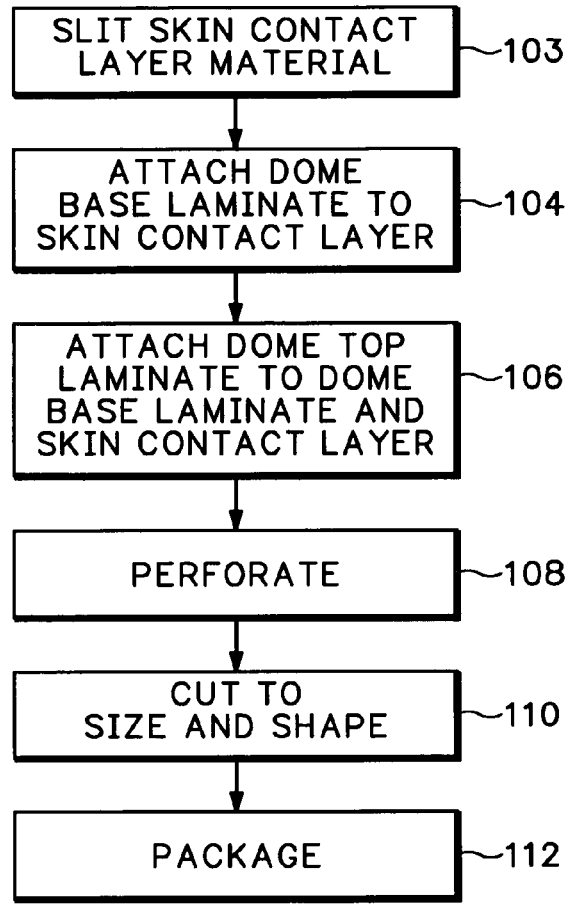
FIG. 9 is a flow diagram showing further steps according to the method of the present invention for manufacturing the bandage shown in FIG. 1.

As shown in FIG. 9, the bandages are assembled using a rotary converter such as the one described previously. First, a web of the required material for the skin contact layer 16 is slit to a width such as about 76 mm (3 in), wide enough to encompass the length 24 of the bandage 14, as indicated at 103.

Next, the dome base laminate of layers 36 and 40 formed as mentioned above at 102 is applied to the skin contact layer 16 by appropriately removing any carrier or liner from the layer 40 of transfer adhesive material, and the dome base layer 38 is placed on the skin contact layer 16 and fastened to it by the action of the adhesive layer 40, as shown at 104. The dome base layer 38 is aligned with a middle part of the skin contact layer web, so that its straight margins 52 face toward the sides of the slit web of skin contact layer material and are parallel with the length of that web of skin contact layer material.

Next, as noted at 106, the previously fabricated dome top laminate of domes 28, skirt portions 42, and adhesive layer 44 is attached to the dome base layer 38 and the skin contact layer 36 in proper alignment with the dome base layer 38, so that the straight margins 58 of the dome top layer 36 are located outside the straight margins 52 of the dome base layer and parallel with them. The skirt portion 42 of the dome top layer 36 is thus attached by the adhesive layer 44 both to the dome base layer 38 and to the carrier layer 16, where the margins 58 of the dome top layer 36 extend beyond the straight margins 52 of the dome base layer 38.

After the dome top layer 36 is attached to the dome base layer 38 and skin contact layer 16, each bandage 14 is appropriately perforated, 108, preferably by a sonic perforating machine associated with the converter. For example, a suitable sonic perforator is available from Branson Ultrasonic Corporation, of Danbury, Conn. The individual bandages 14 are then cut to finished size and shape, and the cut 22 is made in the liner 20, as shown at 110, preferably by die cutting, using the rotary converter. Alternatively, the liner 20 can be removed and replaced by a combination of liner portions of which one includes a margin folded back as a flap 23, shown in broken line in FIG. 1, before the individual bandages 14 are cut to finished size and shape.

The bandages 14 are then released from the surrounding areas of the laminated webs of skin contact layer 16, dome base layer 38, and dome top layer 36, and as noted at 112 the individual bandages are appropriately packaged.

Figure 10:
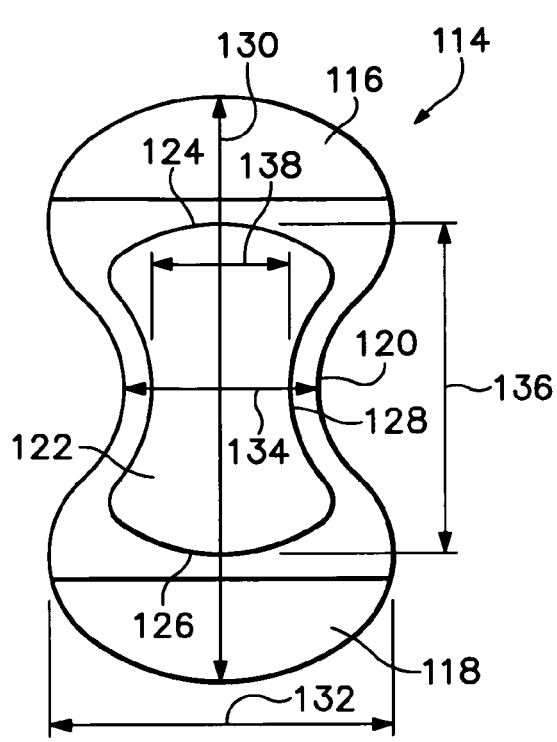
FIG. 10 is a top plan view of an alternative embodiment of the bandage.

Referring next to FIG. 10, a bandage 114 is of similar construction to the bandage 14, but is of a different shape, resembling a figure-of-eight having a pair of enlarged end portions 116 and 118 and a narrow waist portion 120. A dome 122 of the bandage 114 also has a pair of convexly arcuate end portions 124 and 126 that are interconnected by a narrower waist portion 128. Such a bandage 114 is intended principally for use to protect convex portions of one's anatomy, such as elbows, heels, fingers, and toes, and can be made in a range of sizes, with a preferred overall length 130 of 57 mm (2.25 in.) and an overall width 132 of 31.75 mm (1.25 in.), with a waist width 134 of 22.23 mm (0.875 in.). The overall length 130 and overall width 132 could be varied within a range of at least ½ in.

The dome 122 is significantly shorter than the overall length 130 to provide ample adhesive-carrying area in the end portions 124 and 126 of the skin contact layer, to attach the bandage securely to a person's skin. The dome 122 thus has a preferred overall length 136 of about 35 mm (1.375 in.) and an overall width 138 of about 12.7 mm (0.5 in.), although both of these dimensions could be varied within a range of at least 6.3 mm (0.25 in.). The height of such a dome could be within the range of 4-6 mm. (0.18-0.25 in.).

Figure 11:
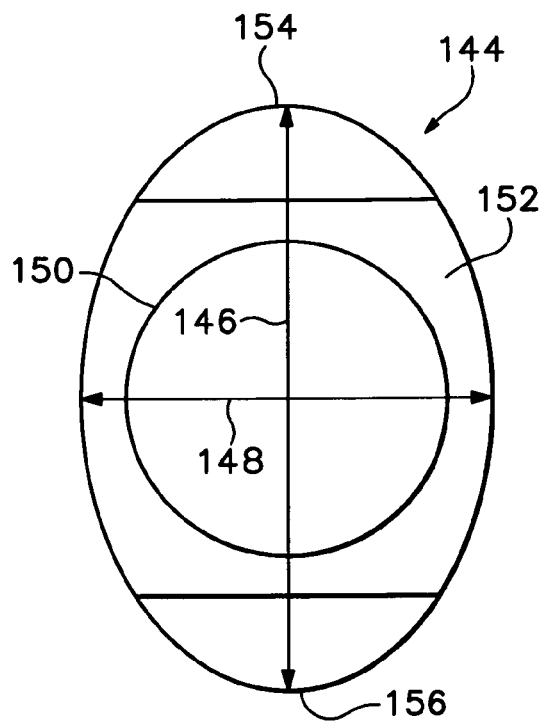
FIG. 11 is a top plan view of another alternative embodiment of the bandage.

Referring next to FIG. 11, a bandage 144 has an oval shape and may be elliptical, for example, with an overall length 146 of 108 mm (4.25 in.) and an overall width 148 of 76.2 mm (3 in.), both of which could be varied by as much as 19 mm (0.75 in.). A centrally located circular dome 150, whose diameter is preferably about 57.2 mm (2.25 in.), or could be varied within 9.5 mm (⅜ in.) of that size, is provided to correspond with the length 146 and width 148 of the bandage 144. The bandage 144 has an amply wide skirt portion 152 surrounding the dome 150 and also has some extension of a suitably flexible and elastic skin contact layer at each of the ends 154 and 156. The larger size of the bandage 144 by comparison with the previously described bandages 14 and 114 makes the bandage 144 more appropriate for use in prevention and treatment of pressure ulcers. The bandage 144 is preferably manufactured of film materials and adhesives such as those described above, or of variations of those materials having a different moisture vapor transference rate. Such a bandage could be used in locations such as a person's sacrum (lower back), greater trochanter (hip), gluteus maximus (buttocks), heels, or elbows.

The bandage could also be produced with the dome and skin contact layer in other shapes to be used in other particular applications, without departing from the invention.

Figure 12:
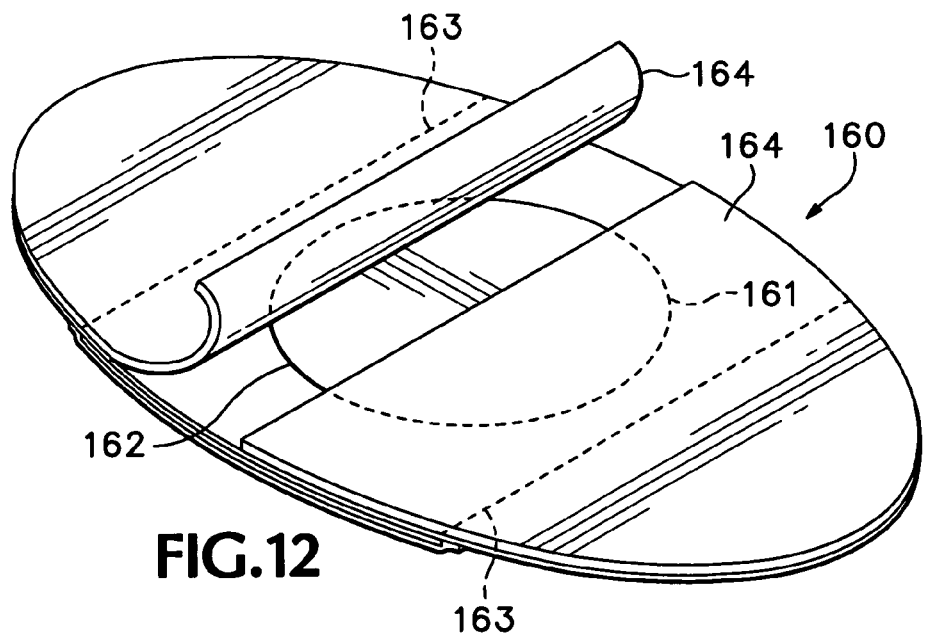
FIG. 12 is a partially cutaway isometric view taken from the bottom side of yet another alternative embodiment of the bandage.

The size of the bandage 14 could also be varied, keeping the same proportions to provide a bandage 14 whose size is, for example, 20 percent larger or 40 percent larger than previously mentioned, in order to protect an area of a patient's skin with an appropriately large bandage.

Where skin that is already blistered or abraded is to be treated to enhance healing of such skin, a bandage 160 shown in FIG. 12, may be utilized. Although the bandage 160 may generally be similar to the bandage 14, in an area 161 corresponding generally in size and shape to the dome, and optionally including the area 163 of the skirt portion of the dome top layer and the area of the dome base layer, the adhesive carrying lower or second side of the skin contact layer may be left without a layer of adhesive, or may be provided with a layer 162 of an adhesive translucent, flexible hydrocolloid material. Such a hydrocolloid material, once the liner 164 has been removed from the bandage, is placed in contact with the patient's sore or abraded skin or other wound and can absorb wound exudate, promote a moist wound-healing environment, and provide cushioning. Such a hydrocolloid material is available, for example, from Avery Dennison Medical, of Mentor, Ohio, as its MED 2190H, an 18 mil hydrocolloid, low peel force, transfer adhesive tape. Similar material may also be used in various thicknesses in a range of 10 to 50 mils for various applications.

A device embodying the present invention could also be applied to a surface of a device or an article of clothing, rather than to the user's skin. For example, a layer of a suitable material corresponding to the skin-contact layer 16 could be attached by sewing, or other bonding technique, i.e., heat or ultrasound, to the inside of a user's apparel, i.e., underwear, sock or shoe. It could also be attached to the inside of a shoulder pad, elbow pad or backpack strap, etc., for use in athletic or recreational activities.

In order to deal with other possible circumstances, friction reducing devices embodying the present invention could be incorporated into many articles during original manufacture of such articles, such as hospital mattress covers, wheelchair cushions, bicycle seats, shoe inserts, removable heel counters for shoes, other locations in the interior of shoes, socks, undergarments, straps for undergarments, and backpacks.

Figure 13:
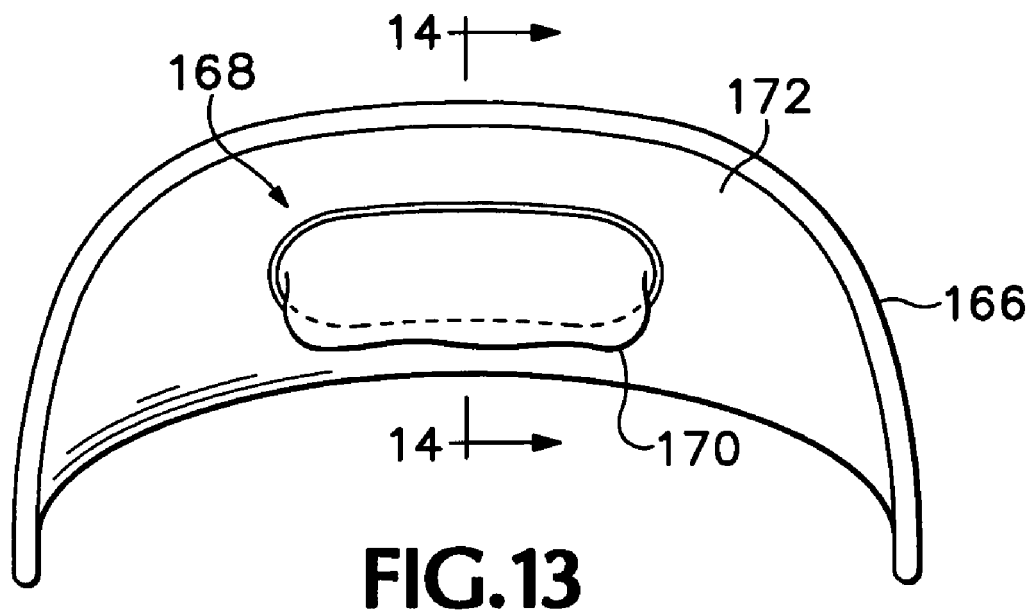
FIG. 13 is a perspective view from the upper front side of a heel counter insert for use in a sports shoe, including a friction reducing device according to the present disclosure.
Figure 14:
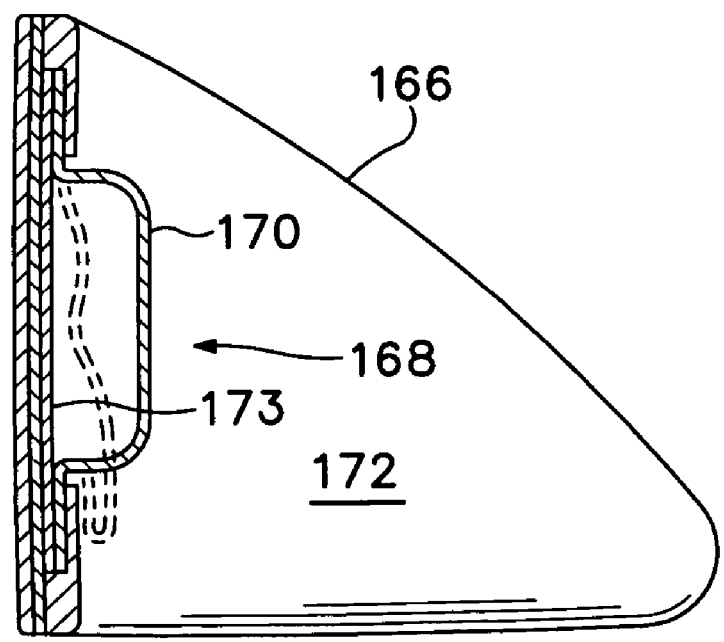
FIG. 14 is a sectional view of the heel counter insert shown in FIG. 13, taken along line 14-14 of FIG. 13.

For example, FIGS. 13 and 14 show a removable heel counter 166 for a sports shoe, incorporating a friction reducing device 168 according to the present invention in which a dome 170 is exposed on an inward-facing surface 172 of the removable heel counter 166. The friction reducing device 168 may also include a dome base layer 173, between the dome 170 and a dome supporting layer 174. The dome base layer 173 would be attached to the dome supporting layer 174 and be of material over which the dome 170 can glide freely. The friction reducing device 168 thus incorporates structures capable of performing the function of a friction reducing bandage 14, as described above, in the supporting structure of a heel counter 166, which may be a removable shoe accessory or a permanent part of a shoe.

The dome supporting layer 174 of such a friction reducing device 168 corresponds to the skin contact layer 16 of the bandage shown in FIGS. 1-5 and may be of a thicker material, and may be thermally laminated into the structure of the heel counter 166 itself. If a dome base layer 173 is not included, the dome supporting layer 174 should be of material that would not interfere with the gliding motion of the dome top layer 170. Instead of the thin polyurethane film material of the skin contact layer 16, the supporting layer 174 is preferably of a thicker film or may be of a durable, sturdy textile fabric, such as a woven cloth or knitted textile material, or of a different plastic such as a film or sheet of polyamide or polyester compatible with the adjacent material of the rest of the heel counter 166, since greater durability than for a bandage is preferred.

Figure 15:
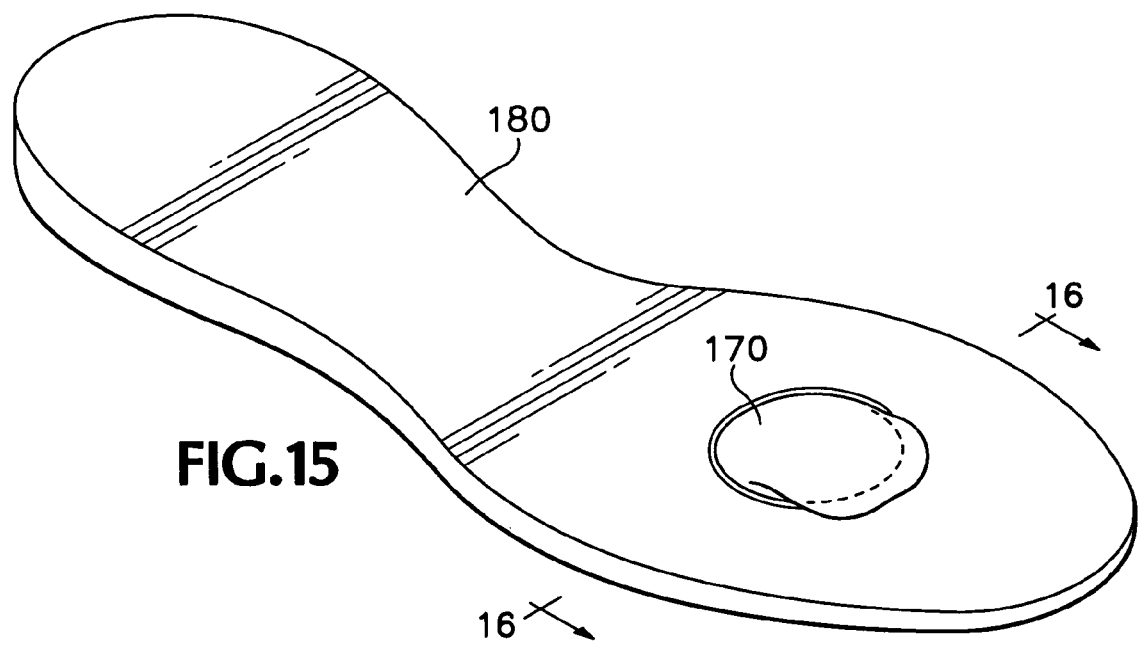
FIG. 15 is a perspective view of an insole, including a friction reducing device according to the present disclosure.
Figure 16:
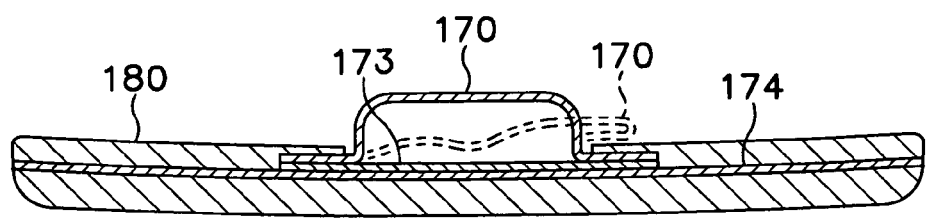
FIG. 16 is a sectional view of the insole shown in FIG. 15, taken along line 16-16 of FIG. 15.

In a different article such as a replaceable accessory insole 180, shown in FIGS. 15 and 16, the supporting layer 174 could also be of a plastic material such as polyurethane, suitable to be molded into, or inserted between other layers of the structure of the article concerned, to provide a secure incorporation of a friction reducing device 182 according to the present invention. The friction reducing device 182 also includes a dome 170 which is carried by a supporting layer 174 and exposed to be contacted by the user's foot to function in the same way as the dome 28.

The friction reducing domes 170 can be manufactured in generally the same fashion as that described above with respect to the bandage 14, with modifications as necessary to the supporting layer 174 depending on the article in which the friction reducing device is being incorporated.

Figure 17:
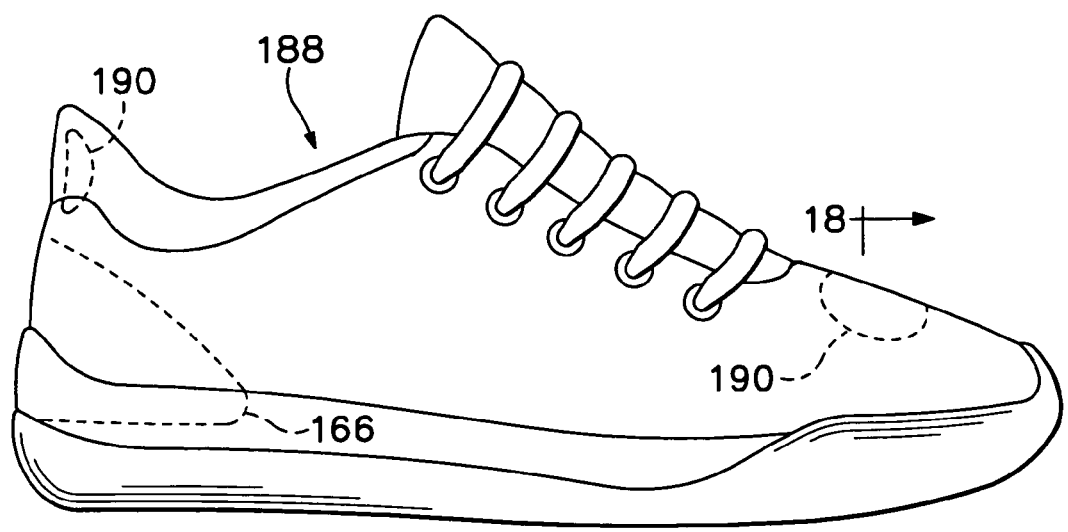
FIG. 17 is a side elevational view of a sports shoe incorporating friction reducing devices.
Figure 18:
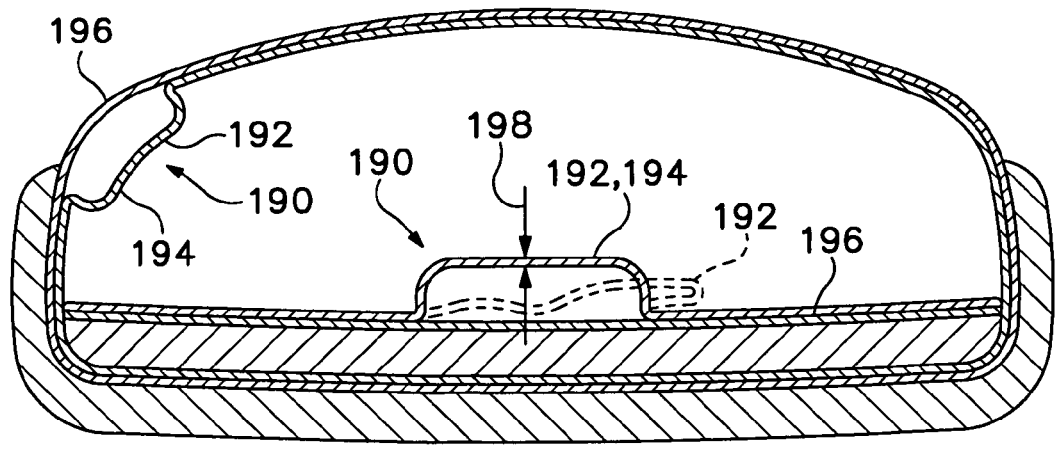
FIG. 18 is a sectional view taken along line 18-18 of FIG. 17.

As shown in FIGS. 17 and 18, as an example of including a similar friction reducing device in an article of sports equipment or other application such as those mentioned above, a shoe 188 may incorporate friction reducing devices 190 each including an integral dome 192 that functions in generally the same way as the dome 28. The friction reducing device 190 may be located in a permanently included heel counter portion of the shoe, in a heel collar, in the permanent insole, or at another critical place in the upper of such a shoe 188.

In order to ensure reasonably long durability of the friction reducing device 190 incorporated in an article of clothing or sports or other equipment such as the shoe 188, a dome top layer 194 and dome base layer 196 may be made of a flexible material of greater strength than the 25 microns-thick polyethylene film used as the dome top layer 36 of the bandage 14 described above. For example, a polyethylene film material having a greater thickness 198, in the range of 25 microns to 1.525 mm (1-60 mils) would be satisfactory. Instead of polyethylene, another polymeric material such as a polyester film or a soft and closely woven or knitted textile fabric might be used, although it might require the use of a small amount of a lubricant between the dome top layer 194 and the dome base layer 196. More preferably, the top layer 194 and bottom layer 196 are appropriately formed and interconnected portions of the textile fabric, plastic-impregnated fabric, or plastic film of which the shoe 188 or other article is constructed, thin enough to be easily flexible, and lubricated as necessary to be able to slip readily along each other. Such formation and interconnection of the layers of material to form the domes 192 is performed as part of the process of assembling the article including the domes 192.

Referring next to FIGS. 19-29, an articulated mechanical arm 200 includes a pair of elongate straight segments 202 and 204 interconnected with each other by a hinge joint 206. A pair of cables 208 and 210 extend respectively along the top and bottom of the mechanical arm 200 and are held in position by respective guides 212 including holes through which the cables 208 and 210 extend. The cables 208 and 210 are moveable longitudinally through the guides 212 as shown by arrows 214 in connection with movement of the arm, and may be moved longitudinally in connection with movement of a device mounted on the arm 200. By such movement through the guides 212 the cables 208 and 210 necessarily rub against the interior surfaces defining the holes in the guides 212, and in order to counteract the friction thereby created, the cables 208 and 210 are equipped with friction reducing protective devices 216 shown in FIG. 20.

Figure 20:
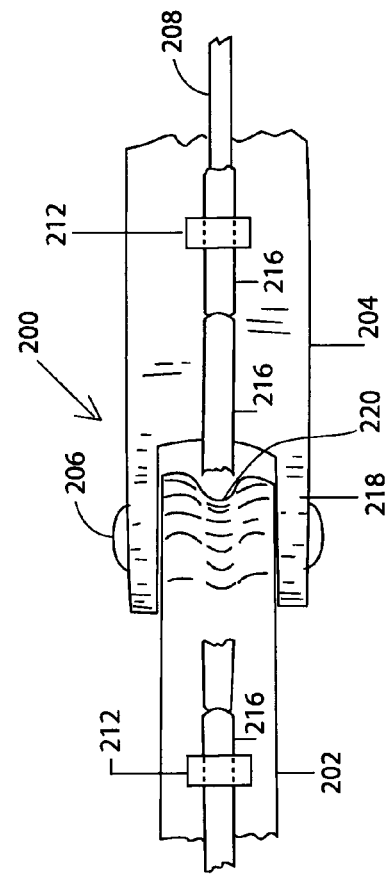
FIG. 20 is a view, at an enlarged scale, of the articulated mechanical arm shown in FIG. 19, taken in the direction indicated by the line 20-20 in FIG. 19.
Figure 19:
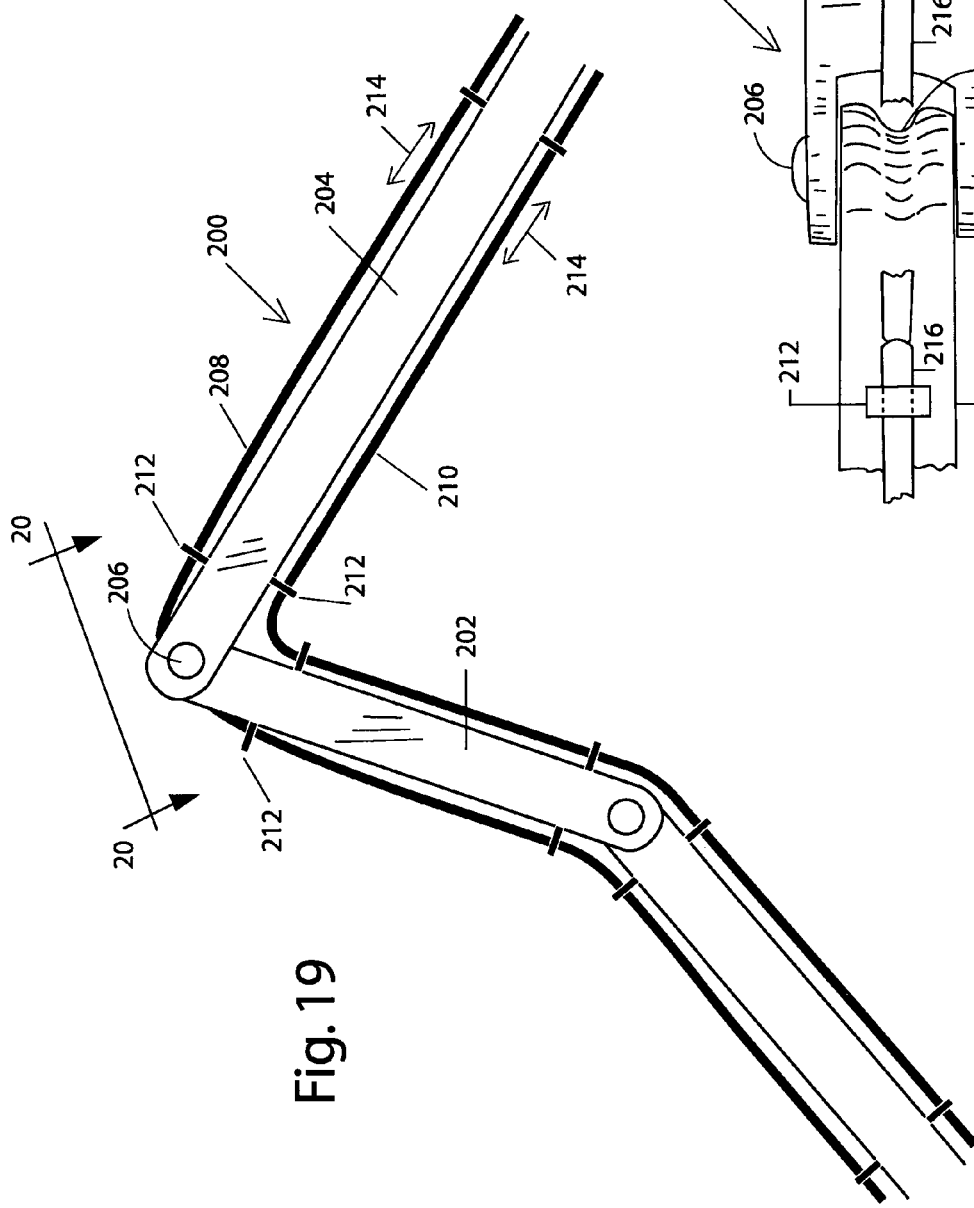
FIG. 19 is a side elevational view of an articulated mechanical arm having cables equipped with a friction reducing device.

It may be seen in FIG. 20 that the hinge joint 206 includes a fork 218 included in the segment 204 of the mechanical arm 200, and the end of the segment 202 fits between the sides of the fork 218. A groove 220 may be formed in the end of the segment 202 of the arm, where it fits between the sides of the fork 218. The groove 220 is provided to support and guide the cable 208 when the arm segments 202 and 204 are located at an angle with respect to each other as shown in FIG. 19. Movement of the cable 208 along the surfaces defining the groove 220 and the surfaces alongside the groove 220 may impose forces in a longitudinal or circumferential direction against the cable 208 or a friction reducing device 216 in place on the cable 208. In FIG. 20 the cable 208 is cut away to expose the end of the segment 202 and the groove 220 defined therein, for the sake of clarity.

Referring to FIG. 21, a length of cable 222 is shown equipped with a friction reducing protective device 216 similar to those shown in FIG. 20. With the cable 222 shown suspended and extending horizontally or as if it were resting on a horizontal surface, the friction reducing device 216 is in a relaxed, neutral, position in which an outer surface 224 may be generally cylindrical and opposite ends 226 and 228 may be oriented generally transversely with respect to the length of the cable 222.

An inner, supporting, layer 231 closely surrounds the cable 222 and is fastened securely thereto so as not to be free to rotate around the cable 222 or to slide longitudinally along the cable 222. Fastening the inner layer 231 to the cable 222 may be accomplished by any of various means including use of an adhesive, chemically or thermally causing a tubular sleeve to shrink onto the cable 222, or by extruding the material of the inner layer 231 around the cable 222. Alternatively, depending partly on the material of the cable, it may be practical to apply the inner layer 231 by dipping the cable 222 into a suitable plastics material in a melted or dissolved form. It will be appreciated that different materials for and manners of securing the inner layer 231 to the cable 222 may depend upon the construction and size of the cable. It is contemplated that the friction reducing device 216 may be utilized with cables or cords of a wide variety of sizes and made of various different materials such as braided or woven natural or synthetic fibers, or wire, as well as twisted wire strand cables. Depending upon the chemical composition of synthetic fiber cables certain materials for the inner layer 231 may be more or less appropriate and may be able to be fastened in place in one manner or another more efficiently or more securely.

When the friction reducing device 216 has been in contact with an object, such as one of the guides 212, for example, while the cable 222 is moved in a leftward direction as indicated by the arrow 230 in FIG. 22, the opposite ends 226 and 228 of the friction reducing device 216 may assume the appearance illustrated in FIG. 22. This appearance results from movement of an outer layer 232, shown best in FIG. 25, relative to the cable 222 toward the right, opposite the arrow 230, as shown in FIG. 22.

As a result of such relative movement of the outer layer 232 of the friction reducing device 216 with respect to the cable 222, the right-hand end 228 may appear as shown in FIG. 23 as a sleeve, bloused outward and extending outward radially about the cable 222. A skirt or marginal portion of the outer layer 232 may thus be gathered inward and may extend within a portion of itself, as an inverted portion 234.

Figure 24:
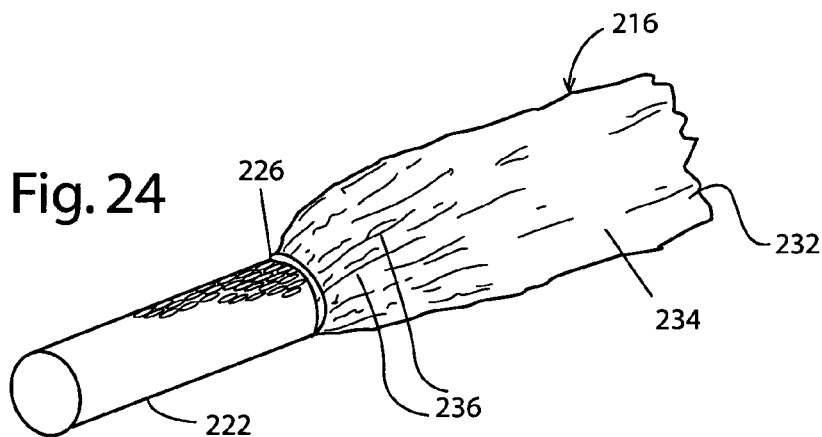
FIG. 24 is a perspective view of the left end of the portion of a cable and friction reducing protective device shown in FIG. 22.

At the opposite, or left, end 226 of the friction reducing device 216 the outer layer 232, as shown best in FIG. 24, may extend snugly and with a reduced diameter along the cable 222. At the same time, the outer layer 232 may be drawn into wrinkles or folds extending longitudinally along the cable 222 away from the left end 226, as the outer layer 232 is moved generally away from the attachment of the left end 226 of the friction reducing device 216 to the cable 222. Thus, generally longitudinal folds 236 may appear in the material of the outer layer 232, extending for a distance from the end 226 toward the opposite end 228 of the friction reducing device 216.

Figure 25:
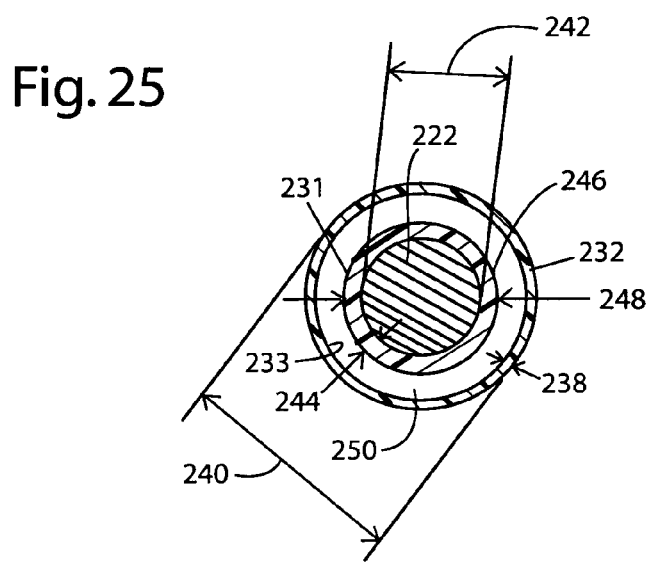
FIG. 25 is a sectional view, at an enlarged scale, taken along line 25-25 of FIG. 21.

This can occur because of the construction of the friction reducing device 216, as is further shown in section view in FIG. 25. The outer layer 232 may be a flexible thin-walled tube of, for example, an extruded polymeric plastic material. The outer layer 232 may have a wall thickness 238 of, for example, 0.002 inch-0.020 inch, and in a friction reducing device 216 intended for use with a cable 222 having a diameter 242 of 0.125 inch, may have a diameter 240 of about 0.56 inch, with a wall thickness of 0.004 inch.

The inner layer 231 may be thicker than the outer layer 232 and so may have a radial thickness 244 of, for example, 0.015 inch-0.075 inch, in order to assure that a surface of the exterior or first side 246 of the inner layer 231 is smooth and free from significant irregularities resulting from the exterior surface shape of the cable 222. As a result, for use with a cable 222 having a diameter 242 of 0.125 inch, with the inner layer 231 having a thickness 244 of 0.025 inch, for example, in place on the cable 222, the inner layer 231 has an outside diameter 248 of 0.175 inch, leaving an annular gap 250 having a radial dimension of about 0.1875 inch, with the outer layer 232 evenly arranged as shown.

While the outer layer 232 is shown herein as spaced loosely apart from the inner layer 231 it may actually be fashioned to lie closely, if not smoothly, along the exterior side 246 of the inner layer 231, either as a result of how assembly is accomplished, or by the outer layer 232 being of material sufficiently pervious to air to permit the outer layer 232 to collapse around the inner layer 231.

As may be seen in FIG. 21 the outer shell or layer 232 is inverted at the end 226 for a distance 252, and it may be inverted at the opposite end 228 over a similar distance. Thus the outer layer 232 includes slack, excess material by comparison with the size and placement of the inner layer 231, and acts as a movable hollow cover over the inner layer 231. The outer layer 232 may thus be moved longitudinally along the cable 222, in or opposite the direction of the arrow 230, until the outer layer 232 is tightened longitudinally as shown in FIGS. 22 and 24, at either the end 226 or the end 228, depending upon the direction in which the outer layer 232 is moved longitudinally along the cable 222. As the outer layer 232 slides along the inner layer 231 the inverted portions may roll to invert more of the outer layer 232 at an end of the device 216 toward which the outer layer 232 is moving, and to evert the layer 232 at the end away from which the outer layer 232 is moved.

Figure 26:
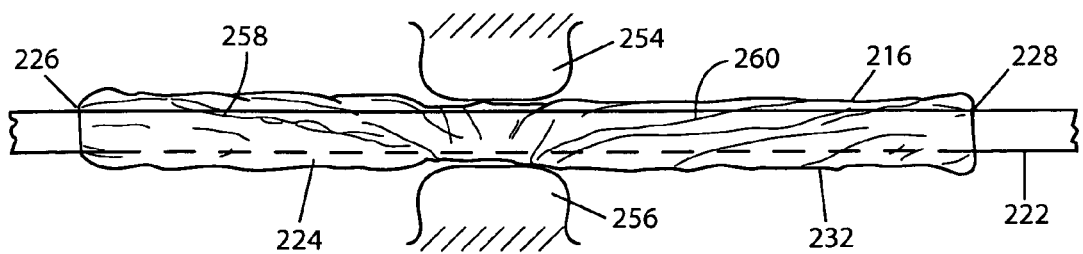
FIG. 26 is a side elevational view of a portion of a cable equipped with a friction reducing protective device as disclosed herein, showing the friction reducing protective device after rotation of the cable with respect to a nearby object in contact with the protective device.

As shown in FIG. 26, in a situation where the cable 222 extends along and generally in contact with an object 254 or between a pair of closely spaced objects 254 and 256 moving with respect to the cable so as effectively to revolve about the cable, the outer layer 232 can move through a certain angle circumferentially about the inner layer 231, to result in the outer layer 232 tending to wrap around the inner layer 231 near the location of contact between the friction reducing device 216 and the objects 254 and 256. So long as the relative rotational movement between the cable 222 and the object or objects 254, 256 amounts to no more than a certain angular rotation before the direction of such movement is reversed, the angular movement can be accommodated by movement of the outer layer 232 around and along the outer face 246 of the inner layer 231. The outer layer 232 may thereby be pulled into a configuration including patterns of wrinkles shaped as opposite helices 258, 260 on opposite sides of the location of the object or objects 254, 256 in which the protected portion of the cable 222 is in proximity or contact. This ability of the outer layer 232 to be wrapped helically about the cable 222 is determined by a combination of the amount by which the circumference of the outer layer 232 exceeds the circumference of the inner layer 231 and the length 252 of the inverted part 234 of the outer layer 232 at each end of the friction reducing device 216.

The ability of the outer layer 232 to slip easily along the inner layer 231 depends in part on the thickness of the outer layer 232 and also upon the material of which the outer layer 232 is constructed. The material may affect both the flexibility of the outer layer 232 and its coefficient of friction against the surface of the outer side 246 of the inner layer 231. Thus a thinner outer layer 232 may more easily be inverted, and the inverted portion 234 may require less space within the end 226 or 228 where it is located, thus contributing to the ease with which the outer layer 232 can slide longitudinally along the inner layer 231. A greater annular gap 250 may similarly contribute to the ease in which the outer layer 232 can move along the inner layer 231, either in a longitudinal direction or in a circumferential direction.

Various polymeric plastics materials may be utilized for the inner layer 231 and the outer layer 232, so long as the two layers have low enough coefficients of friction with respect to each other. For example, polyethylene is a durable, abrasion resistant plastics material which may be sonically welded and easily formed on a cable as the inner layer, so that both the inner and outer layers may be of polyethylene. Where greater elasticity is desirable in the inner layer of a friction reducing device, the inner layer may be of polyurethane, while the outer layer may be of polyethylene, with only a slightly increased coefficient of friction resulting between the inner and outer layers. Some polyvinyls and polyamides and polytetrafluoroethylenes will be suitable, depending on the particular applications, and other plastics materials may also be useful as one or both of the layers 231 and 232. In some cases it may be desired to place a small amount of a lubricating material between the inner layer 231 and the outer layer 232. Such a lubricant should be compatible with the materials of the layers 231 and 232 and for some applications may need to meet requirements as to chemical activity or toxicity, as well.

Figure 27:
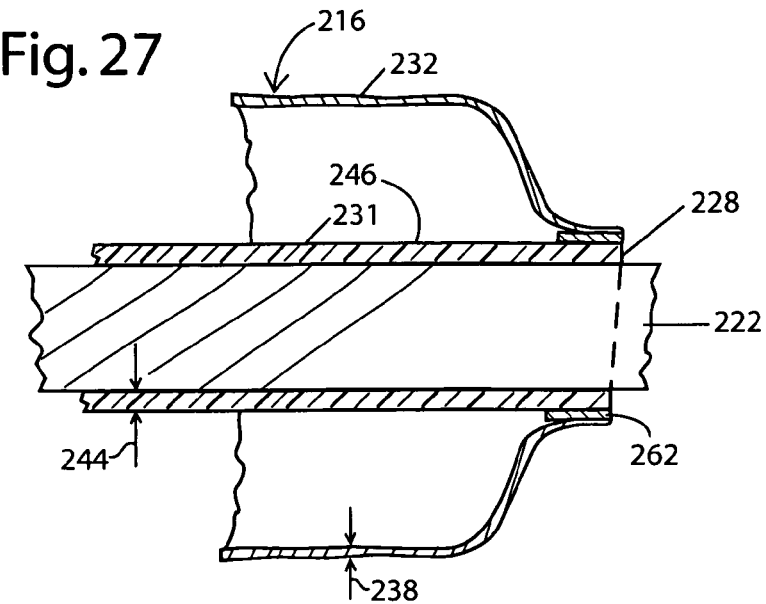
FIG. 27 is a sectional view, taken in the direction indicated by the line 27-27 in FIG. 23, showing the construction of an end of one version of a friction reducing protective device such as those shown in FIGS. 21-26.

Referring to FIG. 27, the outer layer 232 may be attached to the exterior face or outer side 246 of the inner layer by a layer 262 of a suitable adhesive material, which may, for example, be a pressure sensitive adhesive material such as that mentioned with respect to the layer of 40 or 44 of transfer adhesive utilized in the bandage 14. Alternatively, the adhesive 262 might be a chemical adhesive utilized to weld together the confronting surfaces of the outer layer 232 and inner layer 231.

The friction reducing device 216 may be assembled with the cable 222 by first installing the inner layer 231 using one of the previously mentioned techniques, and by thereafter sliding an open-ended tube of material for the outer layer 232 along the cable 222 until the layer 232 surrounds the inner layer 231. With a strip of the adhesive material 262 of a desired size in place around the exterior of the interior layer 231, the end of the outer layer 232 can be gathered inward as a skirt and adhered to the adhesive material 262 to form the closed end 228 of the friction reducing device 216. With a length of the tubular material of the outer layer 232, exceeding the length 263 of the inner layer 231 by a desired amount surrounding the inner layer 231, the opposite end 226 of the friction reducing device 216 may be assembled in the same fashion. Thus, when the excess length of the tubular material of the outer layer 232 is straightened out by pulling it toward both of the ends 226 and 228 the result will be configuration similar to that shown in FIG. 21, with inverted portions 234 at both ends of the device 216.

Figure 28:
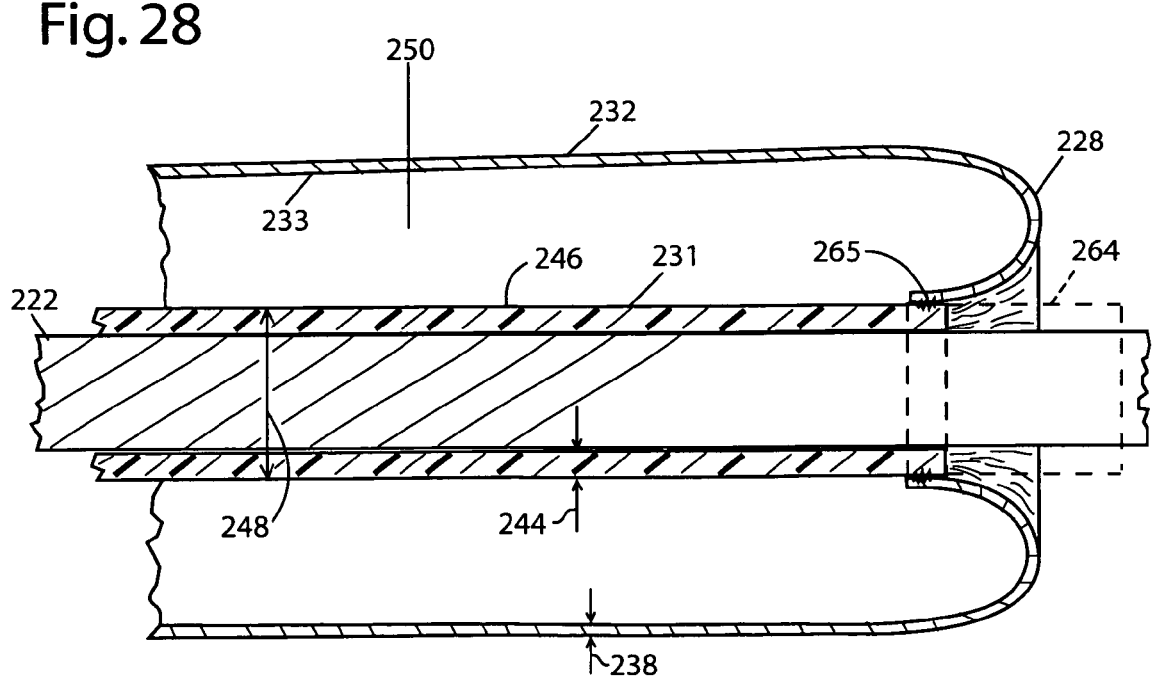
FIG. 28 is a sectional view taken in a direction similar to that of FIG. 27, showing the construction of an end of an alternative embodiment of a friction reducing protective device.

As shown in FIG. 28, the outer layer 232 may, alternatively, be sonically welded to the exterior surface of the inner layer 231 if the materials of the inner layer 231 and the outer layer 232 are compatible and thermally weldable to each other. As shown in FIG. 28 the material of the outer layer 232 has been inverted prior to such sonic welding, although it may in may instances be more convenient to perform the sonic welding operation without first inverting the end of the tubular material of the outer layer 232. In that case the unwelded portion of the outer layer 232 can be folded back around the welded portions in a configuration similar to that shown in the cutaway portion of FIG. 21.

As also shown in FIG. 28, the end of the material of the outer layer 232 need not be attached at the extreme end of the inner layer 231. Instead, the inner layer 231 may extend a desired distance beyond the attachment of the outer layer 232, as illustrated in broken line at 264 in FIG. 28. With such an extended portion of the inner layer 231 available the portion 234 of the outer layer 232 which may be inverted at either end of the friction reducing device 216 can be protected from contact against the surface of a cable 222 which may be rough or otherwise may tend to abrade the material of the outer layer 232.

Figure 29:
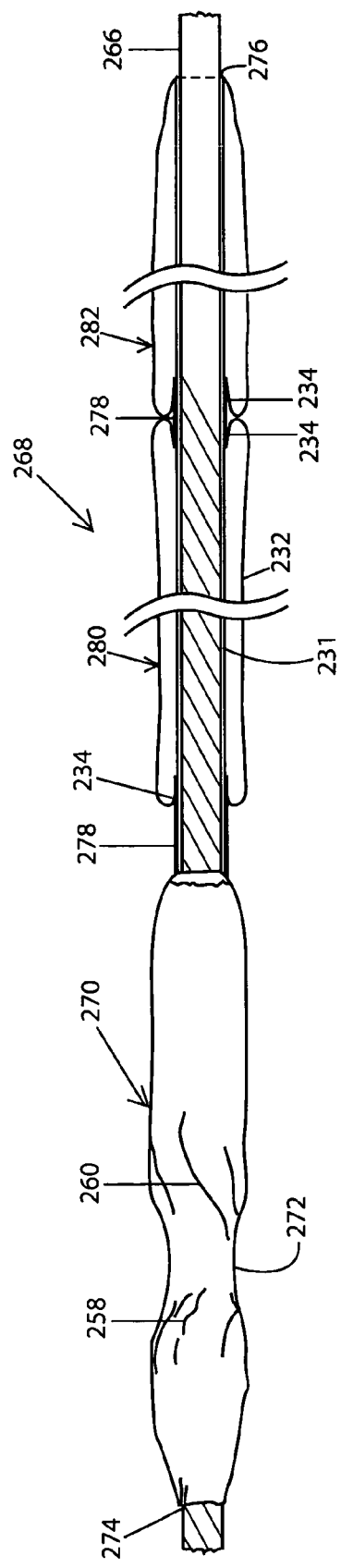
FIG. 29 is a side elevational view, partially cutaway, showing a length of a cable equipped with a friction reducing protective device including several segments.

In situations where a long segment of a cable may be subject to contact with adjacent surfaces against which it is undesirable for the cable to rub, a cable 266 such as is shown in FIG. 29 may be protected by a friction reducing device 268 including several adjacent segments 270, 280, and 282, each similar to a friction reducing device 216. As shown in FIG. 29, a first segment 270 is shown in a condition of having been circumferentially pulled around the cable 266 in a central portion 272, thus pulling the material of the outer layer 232 longitudinally toward the portion 272.

As shown in the cutaway portion of FIG. 29, the inner layer 231 is continuous along the entire friction reducing device 268 from its first end 274 to its opposite end 276. Between the ends of adjacent segments 270 and 280, as at 278, the outer layer 232 is gathered radially inward and securely attached to the inner layer 231. An inverted portion 234 of the outer layer 232 is present at each of the opposite ends of the segment 280, which is shown in a generally relaxed condition, not showing effects of having been in contact with any external surface during recent longitudinal or rotational movement of the cable 266. As a result, the gathered and attached portion 278 between the segments 270 and 280 is partially exposed and visible.

In contrast, at the opposite end of the segment 280, between the segment 280 and the adjacent segment 282, the attached portion 278 of the outer layer 232 is hidden within the inverted portions 234 of the adjacent segments 280 and 282. The outer layer 232 of the segment 282 is shown as having moved longitudinally along the cable 266 toward the segment 280, lengthening the inverted portion 234 of the segment 282 at its end adjacent to the segment 280. At the same time, that movement of the outer layer 232 in the segment 282 has straightened the material of the outer layer 232 of the segment 282, placing it under some slight amount of tension longitudinally and gathering it toward the inner layer 231 at the end 276 of the friction reducing device 268.

It will be understood that the number of adjacent segments of such an extended friction reducing device 268 is not limited to three such segments 270, 280, and 282, which have been shown herein for convenience. Construction of such an extended friction reducing device 268 is similar to that described above in connection with description of the friction reducing device 216. That is, the inner layer 231 is first constructed and placed upon, or formed upon, the cable 266 to be protected. Thereafter, beginning at one end of the friction reducing device 268 a suitable length of tubular material for the outer layer 232 may be placed or formed around the inner layer 231 and there gathered inwardly and fastened to the inner layer 231. Thereafter, at suitable intervals along the length of the cable 266, and with the length of the tubular material of the outer layer 232 exceeding the length of the corresponding length of cable 266 and inner layer 231, the outer layer 232 may be attached securely to the inner layer 231 using a suitable form of chemical, thermal, or mechanical fastening. Additional segments as desired are similarly made along the remaining length of the inner layer 231 until the desired length of the friction reducing device has been completed.

While an example of the friction reducing device has been described as applied to a cable 222 of a particular diameter, it will be understood that larger or smaller cables can be protected similarly. It will also be understood that not only cables used only in tension, but push-pull devices including solid rods or wires which may be either pulled or pushed during operation may similarly be protected by a device such as the friction reducing protective device 216 or 268 described above. Such devices may be used in many different applications, ranging from the use in protection of very small tension carrying cables of string or thread-like size in miniaturized robotic devices, up to much larger cables utilized in other articulated mechanical applications where protection of a cable or rod is important, as in aircraft control surface operating cables or in robotic devices intended to operate for long periods without attention, as in applications as varied as factory assembly lines or space vehicles.

Figure 30:
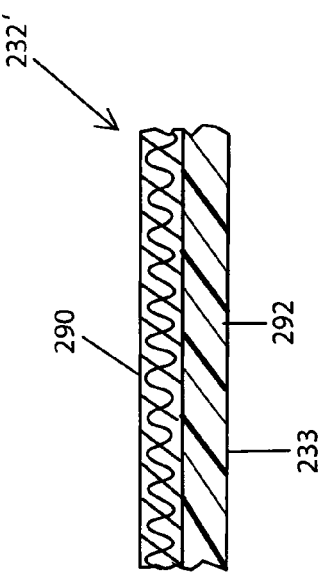
FIG. 30 is a fragmentary sectional view, at an enlarged scale, of material for use as part of a friction reducing protective device.

As shown in FIG. 30, in the case of larger friction reducing devices, it may be desirable to protect the exterior of the friction reducing device itself from abrasion, by providing an exterior surface of a different material intended to provide tensile strength and abrasion resistance yet maintain flexibility, while an opposite, inner surface of such an outer layer provides the required low coefficient of friction. As shown in FIG. 30, then, an outer layer 232' for such a large friction reducing device may include an outer sublayer 290 onto which an inner sublayer 292 of a suitable low-friction plastics material is laminated. Such an outer layer 232' would then be utilized in a friction reducing device with the inner sublayer 292 facing toward the outer surface 246 of the inner layer 231 of such a friction reducing device. Contact between the outer sublayer 290 and adjacent objects along the cable protected by a friction reducing device including such an outer layer 232' would urge the outer layer 232' to move with respect to the inner layer 231, with the low coefficient of friction between the inner sublayer 292 and the exterior surface 246 of the inner layer 231 allowing ease of relative movement of the cable with respect to the adjacent object, taking advantage of the low coefficient of friction between the inner sublayer 292 and the exterior surface 246, within the distance limitations resulting from the relative length and circumference of the outer layer 232' and the inner layer 231 of such a friction reducing device.

With any of the friction reducing devices described above with respect to FIGS. 19-30, movement of a cable with respect to adjacent surfaces of an object with which the cable is associated is possible with a greatly reduced amount of friction, thus avoiding or reducing wear on the surfaces of the cable and of the adjacent object, during movement of the cable within a distance limited by the amount of freedom of the outer layer 232 has to move with respect to the inner layer 231 of the friction reducing device. Even after that distance of low friction movement of the cable has been exceeded, the friction reducing device may be able to move with respect to adjacent surfaces of an object with which the cable is associated with a lower coefficient of friction than would be normal between the surface of the cable and such an adjacent object. Such friction reducing devices as have been described above, then, can reduce the forces necessary to move cables or other control wires or rods, at least through a limited distances, by a significant amount at a relatively small expense for manufacture and installation of such friction reducing devices.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A tubular protective device, comprising:
   (a) a first, tubular, inner, layer of flexible plastics material having opposite first and second sides and a first length;
   (b) a second, tubular, outer, layer of flexible film having opposite inner and outer sides and a second length extending over at least a portion of said first side of said first, inner, layer, said second, outer, layer having a thickness and an inner face, and said second, outer layer being freely movable along said first side of said first, inner, layer through a limited distance determined by locations of attachment of said second, outer, layer to said first, inner, layer, wherein said second length is greater than said first length and a portion of said second, tubular, outer, layer is inverted adjacent an end of said device; and
   (c) wherein said second side of said first, inner, layer is attachable to a surface intended to be protected.

2. The device of claim 1 including a layer of an adhesive material carried on at least a portion of said second side of said first, inner, layer.

3. The device of claim 1 wherein said second, outer, layer is thinner than said first, inner, layer.

4. The device of claim 1 wherein said flexible film of said second, outer, layer is sufficiently pervious to gas that said outer layer is substantially collapsed when said device is in use.

5. The device of claim 1 including a lubricant between said second, outer, layer and said first, inner, layer.

6. In combination with an elongate longitudinally movable force-transmitting article, a tubular friction reducing device, comprising:
   (a) a tubular supporting layer of flexible material having a first, outer, side, an opposite, inner, second side and a first length;
   (b) a hollow tubular cover of flexible material attached to and extending over a portion of said first side of said supporting layer, said hollow cover having a second length greater than said first length, and said lengths being parallel, the hollow cover being freely movable along said first side of said supporting layer through a distance related to an amount by which said second length is greater than said first length; and
   (c) said tubular supporting layer being disposed along and surrounding a portion of said force transmitting article with said second side of said supporting layer being securely attached to said portion of said article so that said hollow cover is exposed toward a surface from which said article is intended to be protected.

7. The combination of claim 6 wherein the article is a cable.

8. The combination of claim 6 wherein the article is a rod.

9. The combination of claim 6 wherein the article is a wire.

10. The combination of claim 6 wherein the flexible material of the hollow cover includes a polymeric plastic film freely movable into contact with and slidable along said first side of said supporting layer.

11. The combination of claim 6 wherein the flexible material of the hollow cover includes a protective outer layer of textile fabric.

12. The combination of claim 6 wherein said hollow cover extends along said supporting layer surrounding a portion of said length of said force-transmitting article.

13. The combination of claim 6 wherein said supporting layer is attached to said article by an adhesive material.

14. The combination of claim 6 wherein said supporting layer is a heat-shrinkable tube.

15. The combination of claim 6 wherein said supporting layer is formed by dipping said article in a melted plastics material.

16. The combination of claim 6 wherein said supporting layer is formed by being extruded around said article.

17. The device of claim 6 wherein said second, outer, layer is thinner than said first, inner, layer.

18. The device of claim 6 including a lubricant between said second, outer, layer and said first, inner, layer.

* * * * *